(12) United States Patent
Achterrath

(10) Patent No.: US 6,794,370 B2
(45) Date of Patent: Sep. 21, 2004

(54) METHOD FOR TREATING CANCER USING CAMPTOTHECIN DERIVATIVES AND 5-FLUOROURACIL

(75) Inventor: Wolf R. Achterrath, Dectzenbach (DE)

(73) Assignee: Aventis Pharma S.A., Antony Cedex (FR)

( * ) Notice: Subject to any disclaimer, the term of this patent is extended or adjusted under 35 U.S.C. 154(b) by 3 days.

(21) Appl. No.: 10/124,458

(22) Filed: Apr. 18, 2002

(65) Prior Publication Data

US 2002/0111329 A1 Aug. 15, 2002

Related U.S. Application Data

(63) Continuation of application No. 09/559,737, filed on Apr. 28, 2000, now Pat. No. 6,403,569.
(60) Provisional application No. 60/131,678, filed on Apr. 29, 1999.

(51) Int. Cl.[7] .................. A61K 31/7072; A61K 31/525; A61K 31/715; C07H 19/00
(52) U.S. Cl. .................. 514/50; 514/283; 514/274; 514/49; 514/27; 514/251; 514/254.02; 514/24; 514/34; 514/256; 424/193.1; 424/93.21; 424/155.1; 435/325
(58) Field of Search .................. 514/50, 27, 24, 514/34, 251, 254.02, 283, 256, 274, 49; 536/22.1; 424/155.1, 193.1, 93.21; 435/325

(56) References Cited

U.S. PATENT DOCUMENTS 6,403,569 B1 * 6/2002 Achterrath ................... 514/50

OTHER PUBLICATIONS

Pavillard et al. "Combination of Irinotecan (CPT–11) and %–Fluorouracil with an analysis of cellular determinants of drug activity." Biochemical Pharmacology, vol. 56, pp 1315–1322, 1998.*
Armand, Jean–Pierre et al., "Clinical advances with topoisomerase I inhibitors in gastrointestinal malignancies," Anti– Cancer Drugs 10 (Suppl. 1): S5–S12 (1999).
Ducreaux, M. et al., Abstract 823, "Phase I/II study of escalating dose of CPT–11 in combination with LV5FU2 ("De Gramont" regimen) every 2 weeks in the treatment of colorectal cancer (CRC) after 5–FU failure," Proc. of Amer. Soc. Clin. Oncol. 16:234a (1997).
Harstrick, A. et al., Abstract 779, "Phase I study of a weekly schedule of irinotecan (CPT–11), high–dose folinic acid (FA) and 5–fluorouracil (5–FU) as first line chemotherapy (CT) in metastatic colorectal cancer: Final results," Proc. of Amer. Soc. Clin. Oncol. 17:202a (1998).
Nishiyama, M., "Irinotecan (CPT–11) in the treatment of gastrointestinal cancers", Japanese J. Chemotherapy 46(8):292–296 (1998).
Pavillard, V., et al., "Combination of Irinotecan (CPT–11) and 5–Fluorouracil with an Analysis of Cellular Determinants of Drug Activity", Biochemical Pharmacology 56:1315–1322 (1998).
Satlz, L., et al., "CPT–11 (Irinotecan) and 5–Fluorouracil: a Promising Combination for Therapy of Colorectal Cancer", European J. Cancer 32A(Suppl. 3):S24–S31 (1996).
Seitz, J.F. et al., Abstract 261, "Phase I/II study of CPT–11 in combination with LV5FU2 (De Gramont–Regimen) every 2 weeks for the treatment of colorectal cancer (CRC) after 5–FU failure," Annals of Oncology 9(Suppl. 2):68 (1998).
Vanhoefer, U. et al., Abstract 967, "Phase I study of a weekly schedule of irinotecan (CPT–11) in combination with high–dose folinic acid and 5–fluorouracil as first line chemotherapy in patients with advanced colorectal cancer," Proc. of Amer. Soc. Clin. Oncol. 16:272a (1997).

* cited by examiner

Primary Examiner—James O. Wilson
Assistant Examiner—Devesh Khare
(74) Attorney, Agent, or Firm—Balaram Gupta

(57) ABSTRACT

A combination therapy for treating cancer including administering at least one camptothecin derivative in conjunction with another anticancer agent. The combination therapy is preferably used as a first-line therapy for treating metastatic colorectal cancer and preferably involves administration of a combination of CPT-11, 5-fluorouracil and folinic acid, according to specific infusional treatment schedules which show therapeutic synergy in the treatment of cancer.

7 Claims, No Drawings

METHOD FOR TREATING CANCER USING CAMPTOTHECIN DERIVATIVES AND 5-FLUOROURACIL

This application is a continuation of U.S. application Ser. No. 09/559,737, filed Apr. 28, 2002, now U.S. Pat. No. 6,403,569 B1, issued Jun. 11, 2002, which relies on and claims the benefit of the filing date of U.S. provisional application Serial No. 60/131,678, filed Apr. 29, 1999, the entire disclosures of all of which are incorporated herein by reference.

This invention relates to an improved treatment for cancer comprising administering a combination of at least one camptothecin derivative and at least one other colorectal anticancer drug. More specifically, the invention relates to treatments for colorectal cancer comprising administering a synergistic therapeutically effective combination of Campto® (CPT-11, Irinotecan), 5-fluorouracil (5-FU), and folinic acid (FA).

Colorectal cancer is a leading cause of morbidity and mortality with about 300,000 new cases and 200,000 deaths in Europe and the USA each year [Boyle P., Some recent developments in the epidemiology of colorectal cancer In: Bleiberg H., Rougier P., Wilke H. J., eds; Management of colorectal cancer London: Martin Dunitz: 19–34 (1998) and Midgley R. S., Kerr D. J., Systemic adjuvant chemotherapy for colorectal cancer In: Bleiberg H., Rougier P., Wilke H. J., eds.; Management of colorectal cancer: London: Martin Dunitz, 126–137 (1998)]. Although about fifty percent of patients are cured by surgery alone, the other half will eventually die due to metastatic disease, which includes approximately 25% of patients who have evidence of metastases at time of diagnosis.

In the United States, there are currently about 130,000 patients with colorectal cancer, 95,000 with colon cancer and 35,000 with rectal cancer. [American Cancer Society. *Cancer Facts and Figures* 2000.] Of these patients, 20% have metastatic disease at presentation, 40% will ultimately develop metastases, and 57,000 patients will die due to metastatic disease. [Id.].

5-FU has been the mainstay of chemotherapy for colorectal cancer for four decades. It has been shown to improve both survival time (11 months versus 5 months) and quality of life of patients with metastatic disease, when compared to no antitumour therapy [J. Clin. Oncol., 10(6), 904–11 (1992) and Br. Med. J., 306, 752–55 (1993)].

Insights into 5-FU molecular pharmacology have led to several strategies to modulate its cytotoxic effects. Infusional versus bolus administration of 5-FU resulted in a higher response rate (22% v. 14%) but did not significantly effect the median survival time (12.1 months v. 11.3 months). [Meta-analysis Group in Cancer. *J. Clin Oncol.* 1988; 16:301–308.] The most successful approach has been the coadministration of 5-FU with folinic acid (FA), which increases the degree of inhibition of thymidylate synthase [G. J. Peters, C. L. van der Wilt, C. J. van Groeningen et al; Thymidylate synthase inhibition after administration of fluorouracil with or without Leucovorin in colon cancer patients: implications for treatment with fluorouracil; J. Clin Oncol, 12, n° 10: 2035–2042 (1994)], depletes cellular thymidine, and induces apoptosis [C. Benz and E. Cadman; Modulation of 5-fluorouracil metabolism and cytotoxicity by antimetabolite pretreatment in human colorectal adenocarcinoma HCT-8; Cancer Res, 41, 994–999, (1981)]. Folinic acid has been approved in numerous European countries for the treatment of colorectal cancer. Among the various modulations and schedules of administration, high dose infusional regimens of 5-FU plus folinic acid (5-FU/FA) are widely used in Europe and have resulted in the highest response rates (up to 44%) and longest time to progression (around 7 months) and median survival (up to 16.6 months) over administration of bolus 5-FU/FA (J. Clin. Oncol, 15 (2), 808–815 (1997); J. Clin. Oncol, 16(2), 418–426 (1998); Ann of Oncol, (1998); Onkologie, 21,403–307 (1988).

European patent EP 137,145, the disclosure of which is incorporated herein by reference, describes camptothecin derivatives of the formula:

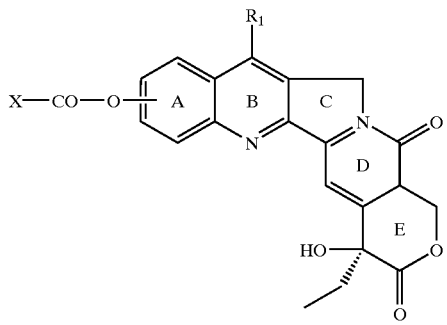

wherein:
  $R_1$ is selected from hydrogen, halogen and alkyl;
  X is selected from a chlorine atom and $NR_2R_3$, wherein $R_2$ and $R_3$, which may be identical or different, are selected from a hydrogen atom, optionally substituted alkyl radicals, carbocycles and heterocycles which are optionally substituted, and optionally substituted alkyl radicals, and form, with the nitrogen atom to which they are attached, a heterocycle optionally containing another heteroatom selected from O, S and/or $NR_4$, $R_4$ being selected from a hydrogen atom and alkyl radicals; and
wherein the group X—CO—O— is located in position 9, 10 or 11 on ring A. These camptothecin derivatives are anticancer agents which inhibit topoisomerase I. CPT-11, also known as Irinotecan, wherein X—CO—O— is [4-(1-piperidino)-1-piperidino]carbonyloxy, is a particularly effective agent in the treatment of solid tumors and, in particular, colorectal cancer.

The European patent application EP 74,256, the disclosure of which is incorporated herein by reference, also describes camptothecin derivatives which are mentioned as anticancer agents, in particular derivatives of structures analogous to the structure given above and in which X—CO—O— is replaced with a radical —X'R' for which X' is O or S and R' is a hydrogen atom or an alkyl or acyl radical.

Other camptothecin derivatives have also been described, for example, in the patents or patent applications EP 56,692, EP 88,642, EP 296,612, EP 321,122, EP 325,247, EP 540, 099, EP 737,686, WO 90/03169, WO 96/37496, WO 96/38146, WO 96/38449, WO 97/00876, U.S. Pat. No. 7,104,894, JP 57 116,015, JP 57 116,074, JP 59 005,188, JP 60 019,790, JP 01 249,777, JP 01 246,287 and JP 91 012,070 or in Canc. Res., 38 (1997) Abst. 1526 or 95 (San Diego-12–16 April), Canc. Res., 55(3), 603–609 (1995) or AFMC Int. Med. Chem. Symp. (1997) Abst. PB-55 (Seoul-27 July–1 August), the disclosure of each of these is incorporated herein by reference.

Camptothecin derivatives are usually administered by injection, more particularly intravenously in the form of a sterile solution or an emulsion. Camptothecin derivatives can also be administered orally, in the form of solid or liquid compositions containing the art recognized adjuvants and/or excipients.

CPT-11, a camptothecin-derivative, is one of the most active new agents in colorectal cancer. In patients resistant to 5-FU, single agent CPT-11 tested in two large phase III randomized trials resulted in a longer survival and a better quality of life compared with supportive care only [D. Cunningham, S. Pyrhönen, R D. James et al, The Lancet, 352, n° 9138, 1413–1418 (1998)]. CPT-11 also resulted in a longer survival without deterioration in quality of life compared with 5-FU/FA infusional regimens [P. Rougier, E. van Cutsem et al The Lancet, 352, n° 9138, 1407–1418 (1998)]. CPT-11 has thus been identified as the reference treatment in metastatic colorectal cancer after failure with prior 5-FU treatment.

CPT-11 has also been shown to be at least as active as the so-called standard 5-FUIFA bolus treatment in chemotherapy naive patients with metastatic colorectal cancer. Single-agent CPT-11, administered intravenously at 125 $mg/m^2$ in two separate studies, resulted in a response rate of 32% and 26% respectively. Median survival was 12.1 months and 11.8 months respectively. [J. Clin Oncol, 14(3), 709–715 (1996); J. Clin Oncol, L15(8) 2910–2919(1997)]. Other studies suggest that CPT-11 may extend survival when used as a second-line therapy in combination with either best supportive care or an infusional based 5-FU regimen. [Cunningham et al. The Lancet. 1998; 352; 1413–18; Rougier et al. The Lancet. 1998; 352; 1407–12.]

A study relating to CPT-11 published by D. Cunningham, Eur. J. Cancer, 32A suppl. 3: S1–8 (1996) suggests that CPT-11 offers a different cytotoxic approach, topoisomerase I inhibition, that may complement the use of 5-FU/folinic acid in colorectal cancer in the future.

In addition, combinations of CPT-11 and 5-FU have already been studied in phase I studies in Japan, indicating in preliminary results that concurrent administration is feasible in terms of safety [L. Saltz et al., Eur. J. Cancer 32A, suppl 3 : S24–31 (1996); Saltz, J. Clin Oncol. 1996, 14:2959–2967; Ducreux, *J. Clin Oncol.* 1999, 17:2901–08; Vanhoefer, J Clin Oncol. 1999, 17:907–13]. At the present time, however, it has never been reported that combinations of CPT-11 and 5-FU can lead to a significant, even therapeutically synergistic increase, of efficacy in the treatment of cancer.

In this application, specific adminstered doses combined with specific schedules of administration of a combination led to a significant increase of efficacy in the expected clinical response. In other words, it is shown that the combination of CPT-II, 5-FU and FA demonstrates therapeutic synergy. A combination manifests therapeutic synergy if it is therapeutically superior to one or the other of the constituents used at its optimum dose.

It has now been found that administering a CPT-11 combination-based therapy according to certain treatment schedules is therapeutically synergistic for the treatment of cancer, particularly colorectal cancer. Specifically, it has been found that a combination of CPT-11, 5-FU, and FA results in an increase in clinical responses greater than expected and higher than for 5-FU/FA alone, whether the combination is administered via a bolus regimen or infusional regimens. The responses are even greater however when the combination is administered by infusion, according to either the AIO treatment schedule, in which the combination is administered weekly, or the de Gramont treatment schedule, in which the combination is administered in two week intervals.

The clinical study which compared the infusional combination CPT-11, 5-FU/FA treatment with 5-FU/FA alone, was conducted in 83 sites, primarily in Europe. Patients were enrolled for the experimental and control arms of both the AIO and de Gramont regimens from May 1997 to February 1998. The survival cut-off date was October 1999, which allowed for a 20-month follow-up of survival-and post-study chemotherapy.

The primary objective of the study was evaluation of the response rate in patients with metastatic colorectal cancer previously untreated with chemotherapy for advanced disease. In addition to response rate, the sample size in the study allowed observation of a significant improvement of time to progression by 50% (6 months versus 9 months). Survival rate, safety, and quality of life were also evaluated.

In setting up this study, at least 338 patients were considered necessary to show a statistically significant difference in response rate between patients treated with 5-FU/FA alone (at least 169 patients) and patients treated with CPT-11 in combination with the same schedule of 5-FU/FA ( at least 169 patents), assuming a 40% improvement in response rate.

Patients were eligible who had a histologically proven adenocarcinoma of the colon or rectum, had unresectable measurable metastases, a perfomance status of 0,1 or 2, had no prior chemotherapy for metastatic disease, had adequate hematologic, renal and hepatic function, and had completed any adjuvant 5-FU treatment more than six months prior to entry into the study. Metastatic colorectal cancer patients who had documented progression after at least one 5-FU regimen for advanced disease were accepted. Prior pelvic radiation was permitted.

In the CPT-11/5-FU/FA arm of the clinical trial, the median age was 62 years old, ranging from 2 to 75; the gender of the patients was 67% female and 33% male; and the performance status of the patients was 52% at 0 and 48% at greater than or equal to 1. Among these patients, the colon was the primary cancer site in 55% of the patients and the rectum in 45% of the patients. For 62% of the patients, the number of organ sites involved was 1 and for the remaining 38%, the number of organ sites involved was greater than or equal to 2. Seventy-seven % of the patients also had liver involvement For these CPT-11 combination-based patients, the median time from initial diagnosis was 4.5 months, the range being 0.1 to 88 months. Twenty-six % had received 5-FU as prior adjuvant therapy; and 20% had received radiotherapy.

In the 5-FU/FA control arm, the median age was 61 years old, ranging from 25 to 75; the gender of the patients was 53% female and 47% male; and the performance status was 51% at 0 and 49% at greater than or equal to 1. In these patients, the colon was the primary cancer site in 65% of the patients and the rectum in 36% of the patients. For 63% of the patients, the number of sites involved was 1, and for 37% of the patients, the number of sites involved was greater than or equal to 2. Eighty percent of the patients also had liver involvement. For these 5-FU/FA patients: (i) the median time from initial diagnosis was 2.7 months, ranging from 0.1 to 104 months. Twenty-four percent had received 5-FU as a prior adjuvant therapy and 16% had received radiotherapy.

Baseline abnormalities for the CPT-11/5-FU/FA population as compared to the 5-FU/FA population was 16% v. 21% had Hgb lesss than 11 g/dL; 47% v. 38% had WBC greater than or equal to $8 \times 10^9$/L; 40% v. 44% had an LDH greater than the upper limit of normal; 7% in each arm had bilirubin greater than the upper limit of normal; and 35% v. 32% had CEA greater than or equal to 100 ng/mL.

Ultimately, the randomized patient enrollment, based on the above criteria, included 395 patients, 199 in the combined CPT-11/5-FU/FA study, and 186 in the 5-FU/FA study. Of the patients receiving CPT-11 based combination therapy, 54 patients were treated according to the AIO regimen and 145 patients were treated according to the de Gramont regimen. Of the patients receiving only 5-FU/FA, 43 patients were treated according to the AIO regimen and 143 patients were treated according to the de Gramont regimen. The therapy was administered as follows:

A. The AIO Treatment Schedule 1. 5-FU/FA+CPT-11 treatment schedule—54 patients

FA 500 mg/m$^2$ i.v. was administered over 2 hours followed by the administration of 5-FU (2300/2600 mg/m$^2$) i.v. infusion over 24 hours, once a week for 6 weeks, which was followed by one week rest. (This seven week cycle is one cycle). For the same cycle, 80 mg/m$^2$ of CPT-11 was administered by i.v. once a week for six weeks, followed by one week of rest. Each cycle was reproduced until a progression (stabilization or improvement in the disease) or unacceptable toxicity was observed.

2. 5-FU/FA treatment schedule—43 patients

FA 500 mg/m$^2$ i.v. was administered over 2 hours followed by the administration of 5-FU (2600 mg/m$^2$) i.v. infusion over 24 hours, once a week for 6 weeks, which was followed by one week rest. Each cycle was reproduced until a progression or unacceptable toxicity was observed.

B. The de Gramont Treatment Schedule 1. 5-FU/FA+CPT-11 treatment schedule—145 patients On day 1, FA 200 mg/m$^2$ i.v. was administered over 2 hours followed by the administration of 400 mg/m$^2$ 5-FU i.v. bolus and 600 mg/m$^2$ 5-FU i.v. over 22 hours (one cycle) and administration of 180 mg/m$^2$ CPT-11 i.v. On day 2, 200 mg/m$^2$ i.v. of FA was administered over 2 hours. This regimen comprised one cycle. The same doses and regimen were given every 2 weeks until a progression or unacceptable toxicity was observed.

2. 5-FU/FA treatment schedule—143 patients

On day 1, FA 200 mg/m$^2$ i.v. was administered over 2 hours followed by the administration of 400 mg/m$^2$ 5-FU i.v. bolus and 600 mg/m$^2$ 5-FU i.v. over 22 hours. On day 2, 200 mg/m$^2$ i.v. of FA was administered over 2 hours. The same doses and regimen were given every 2 weeks until a progression or unacceptable toxicity was observed.

Supportive care was allowed in all treatment schedules and included atropine for the treatment of cholinergic symptons, loperamide for the treatment of late diarrhea, antiemetics for the prophylaxis of nausea and vomiting, and flouroquinolone antibiotic for diarrhea in association with grade 4 neutropenia or neutropenic fever.

Before each infusion during the treatment period, a physical examination, WHO performance status, hematology, and biochemistry were assessed. Radiological assessments to evaluate the antitumor response were performed following every cycle [every 6 weeks for the de Gramont schedule and every 7 weeks for the AIO schedule]. Thus, in-study assessments included:

(i) tumor measurements every six or seven weeks, depending on the regimen;

(ii) evaluation of performance status, weight, quality of life (QLQ-C30), and chemistries on day one of each cycle; and (iii) evaluation of adverse events and CBCs weekly.

A follow-up was also conducted of post-study chemotherapy and survival.

RESULTS

The phase III clinical trial described above demonstrated the therapeutic superiority of combining CPT-11 with 5-FU/FA over 5-FU/FA alone using the same infusional regimens. Both the weekly AIO regimen and the every two weeks de Gramont regimen have shown similar efficacious results with significantly higher response rates and longer time to progression than treatment by bolus administration of 5-FU/FA (J. Clin. Oncol, 15 (2), 808–815 (1997); J. Clin. Oncol, 16(2), 418–426 (1998) ). Therefore, both regimens have established the combination of CPT-11 with 5-FU/FA as the preferred first line treatment of colorectal cancer in Europe.

This phase III randomized study also demonstrated the superiority of combining CPT-11 and 5-FU/FA infusional regimens over the same regimens of 5-FU/FA alone in patients with metastatic colorectal cancer who were previously untreated with palliative chemotherapy. A total of 385 patients were randomized: 199 on CPT-11/5-FU/FA combination therapy and 186 on 5-FU/FA alone. The patient population randomized into this study was representative of the usual patient population with metastatic colorectal cancer suitable for CPT-11 chemotherapy.

A significantly higher response rate was observed with the CPT-11/5-FU/FA combination compared with 5-FU/FA alone: 49% versus 31%. Complete responses occurred only in the CPT-11 combination group in patients with visceral involvement or soft tissue lesions. In a stepwise multivariate analysis, the odds for response in patients receiving the CPT-11 combination was 2.6 times higher than for those receiving 5-FU/FA alone when adjusting for significant covariates (weight loss and time from diagnosis to first metastasis).

A significantly longer duration of response and stabilization was also observed in favor of the CPT-11 combination (8.6 months versus 6.2 months).

Median time to progression (TTP) was also significantly longer with the CPT-11 combination group: 6.7 months versus 4.4 months. In a stepwise multivariate analysis, the risk for progression increased by 62% with 5-FU/FA alone after adjustment for significant covariates (age and liver involvement).

This trial demonstrates a survival advantage which was clinically relevant with a median of 17.4 months with the CPT-11/5-FU/FA combination versus 14.1 months with 5-FU/FA alone. This is among the longest median survival times ever published with combination chemotherapy in metastatic colorectal cancer in a multicentric setting. Further, this significant median survival advantage was obtained despite the fact that further chemotherapy (administered to about 50% of patients) might have lowered the overall survival benefit.

Second line treatment was left to each investigator's decision in the best interest of their patients. In fact, 49% of the CPT-11/5-FU/FA patients received second-line treatment: (i) 2% received CPT-11 based therapy; (ii) 4% received CPT-11 plus 5-FU based therapy; (iii) 32% received 5-FU based therapy; and (iv) 11% received other therapy. In addition, 65% of the 5-FU/FA patients received second-line therapy: (i) 28% received CPT-11 based therapy; (ii) 6% received CPT-11 plus 5-FU based therapy; (iii) 21% received 5-FU based therapy; and (iv) 10% received other therapy. Of note, 34% of patients in the 5-FU/FA group received second line CPT-11 therapy which has been demonstrated to be efficacious. Nevertheless, the difference in survival between the patients on combination therapy as opposed to 5-FU based therapy was still significant, underlining the importance of introducing CPT-11 in first line treatment of patients with advanced colorectal cancer.

Both the weekly AIO and every 2 weeks de Gramont CPT-11 combination regimens were shown to be feasible at the dose and schedule initially planned. The resultant median dose intensity (i.e. the ratio of actual dose intensity relative to planned dose intensity) was actually lower than the planned dose intensity. For CPT-11/5-FU/FA patients under the AOI regimen, the median dose intensity was 0.82 CPT-11 and 0.81 5-FU. For CPT-11 patients under the de Gramont regimen, the median dose intensity was 0.93 CPT-11 and 0.92 5-FU/FA. By contrast, the median dose intensity for 5-FU/FA patients under the AIO regimen was 0.90 5-FU, and for those patients under the de Gramont regimen itn was 0.96 5-FU.

The median duration of treatment was slightly longer in the CPT-11 combination group compared with the 5-FU/FA alone group (5.5 months versus 4.8 months in the weekly AIO regimen and 5.7 months versus 4.2 months in the every two weeks de Gramont regimen, respectively). The number of cycles (7-week duration on the weekly schedule and 6-week duration on the every two weeks schedule) administered at the initial planned dose were comparable between the CPT-11 combination group and the 5-FU/FA group in each schedule (51.1% versus 50.6% on the weekly schedule and 84.6% versus 82.7% on the every 2 weeks schedule).

With respect to adverse events, of the CPT-11/5-FU/FA patient population, 23% had diarrhea, including 17% with grade 3 diarrhea and 6% with grade 4 diarrhea. In addition, 6% of the population had grade 3 or 4 vomiting, 3% had grade 3 or 4 mucositis, 9% had grade 4 neutropenia, 5% had neutropenic fever, and 2% had neutropenic infection. Finally, discontinuations were observed in 9% of the population and drug-related deaths occurred in 0.5% of the population.

This compared to the 5-FU/FA population as follows: 11% had diarrhea, including 7% with grade 3 diarrhea and 4% with grade 4 diarrhea; 6% of the population had grade 3 or 4 vomiting, 2% had grade 3 or 4 mucositis, 9% had grade 4 neutropenia, 5% had neutropenic fever and 2% had neutropenic infection. Finally, discontinuations were observed in 3% of the 5-FU/FA population and no drug-related deaths occurred.

In a comparative bolus study of the combination of CPT-11/5-FU/FA versus 5-FU/FA alone, the median time of survival was 14.8 months for the combination and 12.6 months for 5-FU/FA alone. In this study, CPT-11 was also evaluated alone and the mean survival time was 12.0 months. Thus, administration of the combination by the bolus method, although clearly not as efficacious as the AIO and de Gramont infusional regimens described above, was also therapeutically synergistic, since the combination performed better than either of its component parts.

In summary, the study demonstrated that CPT-11 combination therapy sets a new standard in the first-line treatment of metastatic colorectal cancer, indicating that CPT-11 should be indicated as a component of first-line therapy for patients with metastatic carcinoma of the colon or rectum. More specifically, in this first phase III randomized trial using CPT-11 combination with 5-FU/FA, it was shown that this combination treatment prolongs life without compromising quality of life. Consistent significant advantage in terms of efficacy and clinical benefit i.e., response rate, median TTP, median TTF, median time to PS deterioration, median survival time and quality of life were shown to be in favor of the CPT-11 combination group. No other combination therapy had shown such a high antitumor efficacy over high dose infusional 5-FU/FA regimens at the time of starting this phase III trial.

It is to be understood that in the above-mentioned study, CPT-11 has been administered by i.v. route, but could alternatively be administered by oral route. If administered orally (p.o.) in either of the AIO and de Gramont regimens, CPT-11 would be administered at a dose of 60 to 70 mg/m$^2$ every day for 5 consecutive days, with the same regimen reproduced every three weeks.

Currently, the CPT-11 combination is the only combination regimen in the treatment of metastatic colorectal cancer to demonstrate a survival advantage and a consistency in anti-tumor efficacy over high dose infusional 5-FU/FA. The median survival time of 17.4 months is achieved, with a trend to a better quality of life, by using the CPT-11 combination. This is a significant step forward in the management of patients with metastatic colorectal cancer.

Moreover, the superiority of the CPT-11 combination is achieved with an acceptable and manageable safety profile even though more toxicities occured compared with 5-FU/FA alone. The risks represented by neutropenia and its complications, as well as diarrhea and mucositis are favorably counterbalanced by the high efficacy and better quality of life achieved by the CPT-11/5-FU/FA combination infusional regimens.

Therefore, CPT-11 in combination with 5-FU/FA should be considered as the treatment of choice in first-line treatment of patients with advanced colorectal cancer.

The foregoing written description relates to various embodiments of the present invention. Changes and modifications may be made therein without departing from the spirit and scope of the invention as defined in the following claims.

What is claimed is:

1. A method for treating cancer comprising administration of a combination of at least one camptothecin derivative, 5-fluorouracil (5-FU) and folinic acid to a host in need thereof in an amount and in a schedule of administration that is therapeutically synergistic in the treatment of said cancer.

2. The method of claim 1 wherein the administration of the combination is by infusion.

3. The method according to claim 1, wherein said schedule comprises a cycle of:

administering FA 500 mg/m$^2$ i.v. over 2 hours followed by the administration of 5-FU (from 2300 to 2600 mg/m$^2$) i.v. and 80 mg/m$^2$ of CPT-11 over 24 hours, once a week for 6 weeks, followed by a one week rest; and repeating said cycle until a progression or an unacceptable toxicity is observed.

4. The method according to claim 3, wherein said method is a first-line therapy for metastatic colorectal cancer.

5. The method according to claim 1, wherein said schedule comprises administering a two-week cycle wherein:

200 mg/m$^2$ of folinic acid is administered i.v. over two hours on days one and two of said two-week cycle, 400 mg/m$^2$ of 5-FU is administered by i,v bolus on day one of said two-week cycle and 600 mg/m$^2$ of said 5-FU is administered i.v. over 22 hours on day one of said two-week cycle, and 180 mg/m$^2$ of CPT-11 is administered i.v. on day one of said two week cycle; and said two-week cycle is repeated until a progression or an unacceptable toxicity is observed.

6. The method according to claim 5, wherein said method is a first-line therapy for metastatic colorectal cancer.

7. The method according to claim 1, wherein said at least one camptothecin derivative is administered orally at the dose of from about 60 to 70 mg/m$^2$ daily for five consecutive days, said schedule of CPT-11 administration being reproduced every three weeks.

* * * * *